United States Patent [19]
Yoshioka et al.

[11] Patent Number: 6,056,892
[45] Date of Patent: May 2, 2000

[54] METHOD FOR PURIFYING LIQUID CRYSTAL

[75] Inventors: Yasue Yoshioka; Masahiro Johno; Tomoyuki Yui; Takakiyo Mine, all of Tsukuba, Japan

[73] Assignee: Mitsubishi Gas Chemical Company, Inc., Tokyo, Japan

[21] Appl. No.: 09/034,403

[22] Filed: Mar. 4, 1998

[30] Foreign Application Priority Data

| Mar. 6, 1997 | [JP] | Japan | 9-051629 |
| Aug. 27, 1997 | [JP] | Japan | 9-230978 |
| Aug. 27, 1997 | [JP] | Japan | 9-230979 |

[51] Int. Cl.$^7$ ............................ C09K 19/52; B01D 15/00
[52] U.S. Cl. ........................ 252/299.01; 210/663
[58] Field of Search ................ 252/299.01; 210/663

[56] References Cited

U.S. PATENT DOCUMENTS

| 3,947,375 | 3/1976 | Gray et al. | 252/299.66 X |
| 4,447,655 | 5/1984 | Mendiratta | 568/724 |
| 4,575,412 | 3/1986 | Yudate et al. | 208/45 |
| 4,578,177 | 3/1986 | Yudate et al. | 208/45 |
| 4,874,502 | 10/1989 | Tsuchitani et al. | 208/45 |
| 5,309,263 | 5/1994 | Sato | 359/79 |
| 5,403,511 | 4/1995 | Ohnishi et al. | 252/299.01 |
| 5,540,857 | 7/1996 | Hirai et al. | 252/299.01 |
| 5,559,619 | 9/1996 | Sato | 359/75 |
| 5,849,258 | 12/1998 | Lujano et al. | 423/700 |

FOREIGN PATENT DOCUMENTS

| 0447258 | 9/1991 | European Pat. Off. . |
| 52-59081 | 5/1977 | Japan . |
| 63-261224 | 10/1988 | Japan . |
| 64-87685 | 3/1989 | Japan . |
| 1-48305 | 10/1989 | Japan . |
| 1-281421 | 11/1989 | Japan . |
| 4-13795 | 1/1992 | Japan . |
| 7-72439 | 3/1995 | Japan . |
| 7-181508 | 7/1995 | Japan . |
| 8-193193 | 7/1996 | Japan . |

OTHER PUBLICATIONS

J. Szulc, et al, Investigation of Thermo–and Photostability of Liquid Crystals, SPIE, vol. 1845 Liquid & Solid State Crystals (1992) pp. 481–484.

Chemical Abstracts, vol. 112, No. 6 (1990) Abstract No. 45839C, Abstract of Japanese Laid–Open Patent Publication No. 01–87685 (Mar. 31, 1989).

Chemical Abstracts, vol. 126, No. 3 (1997) Abstract No. 40188μ, Abstract of Japanese Laid–Open Patent Publication No. 08–277391 (Oct. 22, 1996).

Abstract of Japanese Laid–Open Patent Publication No. 52–59081 (May 16, 1977).

Abstract of Japanese Laid–Open Patent Publication No. 63–261224 (Oct. 27, 1988).

Abstract of Japanese Laid–Open Patent Publication No. 4–13795 (Jan. 17, 1992).

*Primary Examiner*—C. H. Kelly
*Attorney, Agent, or Firm*—Sherman and Shalloway

[57] ABSTRACT

A process for purifying an anti-ferroelectric liquid crystal or a ferrielectric liquid crystal, which comprises the following steps 1 to 4, step 1: preparing a liquid crystal solution of an anti-ferroelectric liquid crystal or a ferrielectric liquid crystal to be purified in an aromatic hydrocarbon solvent, step 2; bringing the liquid crystal solution into contact with at least one adsorbent selected from the group consisting of zeolite, alumina and silica gel to separate the liquid crystal solution from the adsorbent, step 3; precision-filtering the resultant liquid crystal solution, and step 4; removing the solvent from an obtained filtrate and recovering a purified liquid crystal, according to which process, there can be easily obtained a high-purity liquid crystal which shows a specific resistance value of at least $5 \times 10^{12}$ Ω·cm and a small thermal decomposition ratio, and which is therefore suitable as a raw material for a liquid crystal display device.

11 Claims, 1 Drawing Sheet

$\rho = K*R$ ($\rho$: specific resistance value (Ωcm))

$K = S/d = 11.3*C$ (C: elecrostatic capacitance (pF) when electrode cell is empty)

$\rho = 22.6*R$ because of C=2pF $\rho = K*R$ ($\rho$: specific resistance value ($\Omega$cm))

$K = S/d = 11.3*C$ (C: elecrostatic capacitance (pF) when electrode cell is empty)

$\rho = 22.6*R$ because of C=2pF

METHOD FOR PURIFYING LIQUID CRYSTAL

The present invention relates to a process for purifying an anti-ferroelectric liquid crystal or a ferrielectric liquid crystal. More specifically, it relates to a process for purifying the above liquid crystals for providing liquid crystals which are excellent in heat stability and electric insulation properties and which give liquid crystal display devices excellent in display qualities and display reliability.

An anti-ferroelectric liquid crystal display device and a ferrielectric liquid crystal display device are attracting attention as liquid crystal display devices which exhibit fast response and are free of viewing angle dependency.

An anti-ferroelectric liquid crystal device is used as a liquid crystal display device which functions according to a simple matrix driving display method, and a ferrielectric liquid crystal device is used as a liquid crystal display device which functions according to an active matrix driving display method.

In general, a liquid crystal material for a liquid crystal display device is required to have a high purity free of chemical impurities. In particular, the presence of ionic impurities is required to be as small as possible.

When a simple matrix driving method is employed, the presence of ionic impurities in a liquid crystal causes mal-switching, i.e., the phenomenon of image sticking, due to the deposition of the ionic impurities on an alignment layer, thereby giving a liquid crystal device having a non-uniformity in the display.

On the other hand, in an active matrix driving method, the presence of ionic impurities causes, besides the above image sticking, the decrease of voltage holding ratio due to leak of electric current ascribed to the ionic impurities, thereby causing reduction in contrast.

When an anti-ferroelectric liquid crystal and a ferrielectric liquid crystal are injected into liquid crystal cells, these liquid crystals are generally injected at a temperature equivalent to, or higher than, a temperature at which these crystals have an isotropic phase because of extremely high viscosity. When the liquid crystals are injected at the above temperature, the liquid crystals are relatively easily thermally decomposed if the liquid crystals contain ionic impurities, acidic substances, basic substances or other impurities.

It is necessary therefore to inhibit the thermal decomposition of the liquid crystal at the step of a liquid crystal panel production, for obtaining a liquid crystal display device having high display reliability. Accordingly, for inhibiting the above thermal decomposition, it is desirable that ionic impurities, acidic substances, basic substances or the like should not be contained, and it is required, at the least, to limit the amount of these impurities to less than a certain amount.

An anti-ferroelectric liquid crystal and a ferrielectric liquid crystal are produced through several steps. In spite of attempts to inhibit the inclusion and formation of the above impurities in the production steps of the above devices, the inclusion of the impurities is unavoidable. In view of the production steps, generally, alkali metal ions, halogen ions, acetate ions, formate ions, etc., are inevitably contained. For removing these ionic impurities from a liquid crystal, the following methods have been proposed.

There are proposed, for example, methods in which as an adsorbent for adsorbing ionic impurities, an ion-exchange resin, a chelate resin, zeolite, alumina, activated carbon or the like is mixed with a liquid crystal to remove ionic impurities (Japanese Patent Publication No. 1-48305 and Japanese Laid-open Patent Publications Nos. 52-59081, 63-261224, 64-87685, 1-281421, 4-13795, 7-72439 and 7-181508), and a method in which ionic impurities are extracted with water under heat (Japanese Laid-open Patent Publication No. 8-193193).

Actually, an anti-ferroelectric liquid crystal and a ferrielectric liquid crystal contain a considerable amount of ionic impurities, and these liquid crystals show a specific resistance value of about $10^{10}$ Ω·cm.

It is considered that the specific resistance value of a liquid crystal is required to be about $10^{12}$ Ω·cm or higher for producing a liquid crystal device which has an excellent display quality, i.e. which is free of the image sticking and non-uniformity in display.

The present inventors have applied the above known purification methods to purify an anti-ferroelectric liquid crystal and a ferrielectric liquid crystal. However, it has been found that these methods give no satisfactory result and that the specific resistance value is increased only up to about $10^{11}$ Ω·cm. Further, there occurs another problem that a liquid crystal undergoes thermal decomposition at the step of producing a liquid crystal panel. It has been further found that some methods, though they produce effects to some degree, are complicated in procedures, and they involve a problem that they do not comply with economic performance if applied industrially. It is therefore necessary to find out a simple and economically effective process.

The present inventors have made diligent studies for overcoming the above problems, and as a result, have found that a high-purity liquid crystal which has a high specific resistance value and is almost free from undergoing thermal decomposition can be obtained by dissolving an anti-ferroelectric liquid crystal or a ferrielectric liquid crystal in an aromatic hydrocarbon solvent to form a liquid crystal solution, bringing the liquid crystal solution into contact with a specific adsorbent, and then precision-filtering the solution. On the basis of the above finding, the present inventors have arrived at the present invention.

That is, according to the present invention, there is provided a process for purifying a liquid crystal, which comprises the following steps 1 to 4, step 1; preparing a liquid crystal solution of an anti-ferroelectric liquid crystal or a ferrielectric liquid crystal to be purified in an aromatic hydrocarbon solvent, step 2; bringing the liquid crystal solution into contact with at least one adsorbent selected from the group consisting of zeolite, alumina and silica gel to separate the liquid crystal solution from the adsorbent, step 3; precision-filtering the resultant liquid crystal solution, and step 4; removing the solvent from an obtained filtrate and recovering a purified liquid crystal.

The present invention will be explained in detail hereinafter.

The liquid crystal to be purified in the present invention is an anti-ferroelectric liquid crystal and a ferrielectric liquid crystal. The liquid crystal to be purified may be an anti-ferroelectric liquid crystal compound or a ferrielectric liquid crystal compound itself, and it may be a composition prepared by incorporating other liquid crystal compound or a compound having no liquid crystal phase to one of the above compounds for improving the characteristics thereof as required. The above liquid crystals to be purified have a smectic phase, and they are therefore generally in an almost solid state.

The liquid crystal compound to which the purification process of the present invention can be preferably applied has the following formula (1). The purification process of the present invention is advantageously applied to an antiferroelectric liquid crystal compound and a ferrielectric liquid crystal compound which are included in the formula (1) and a liquid crystal composition containing one of these.

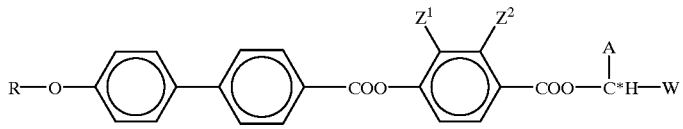

(1)

wherein:
R is a linear alkyl group, preferably a linear alkyl group having 6 to 12 carbon atoms,
each of $Z^1$ and $Z^2$ is a hydrogen atom, or one of $Z^1$ and $Z^2$ is a hydrogen atom and the other is a fluorine atom,
A is —$CH_3$ or —$CF_3$,
C* is an asymmetric carbon atom, and
W is a group of the following (W-1), (W-2), (W-3) or (W-1),
(W-1); —$C_nH_{2n+1}$ in which n is an integer of 4 to 10,
(W-2); —$(CH_2)_m$—O—$CH_{2r+1}$ in which m is an integer of 2 to 8 and r is an integer of 1 to 5,
(W-3); —$(CH_2)_m$—O—$CH_2CH_pF_{3-p}$ in which m is an integer of 2 to 8 and p is an integer of 0 to 3,
(W-4); —$(CH_2)_q$—$CH(C_sH_{2s+1})_2$ in which q is an integer of 0 to 5 and S is an integer of 1 to 5.

The step 1 of the present invention is a step in which the above liquid crystal to be purified is dissolved in an aromatic hydrocarbon solvent to prepare a liquid crystal solution. The solvent used in the step 1 is preferably an aromatic hydrocarbon which can dissolve a liquid crystal to be purified and which hardly absorbs water in air. The solvent is preferably an aromatic hydrocarbon having 6 to 10 carbon atoms. Specific examples of the aromatic hydrocarbon solvent preferably include benzene, toluene, o-xylene, m-xylene and p-xylene, and toluene is particularly preferred. The amount of the aromatic hydrocarbon differs depending upon the kind of a liquid crystal and the kind of the aromatic hydrocarbon, while the amount thereof per part by weight of the liquid crystal is generally 5 to 40 parts by weight, preferably 10 to 30 parts by weight.

The aromatic hydrocarbon used in the step 1 should be a high-grade hydrocarbon having a high purity in view of the object of purification. It is required to use an aromatic hydrocarbon which contains substantially neither ionic impurities nor halogen compounds. The high-purity aromatic hydrocarbon suitable for use in the step 1 can be selected from aromatic hydrocarbons generally called "ultra-pure" grade, which are commercially available. This ultra-pure grade is called "Electronic Grade" in the EL standard of chemicals for use in electronic industries. Specifically, "ultra-pure toluene" can be easily acquired from Kanto Chemical Co., Inc., in Japan.

The temperature for preparing the liquid crystal solution in the step 1 is generally 10 to 70° C., preferably 15 to 50° C., in view of the solubility and the decomposition of a liquid crystal.

The liquid crystal solution prepared in the above step 1 is brought into contact with an adsorbent in the following step 2. Prior to the step 2, the liquid crystal solution from the step 1 may be washed with pure water, and the washing treatment of the liquid crystal solution with pure water is a means preferred for achieving the object of the present invention. The water used for the above washing treatment is preferably pure water from which ionic impurities are removed as much as possible. For preventing the re-contamination with water, the specific resistance value of the water is preferably at least $1 \times 10^7 \Omega \cdot cm$.

The above treatment of washing with water is preferably carried out by a method in which water is added to the liquid crystal solution, the mixing is fully with stirring, and then the water is removed (this method will be referred to as "washing-by-mixing method" hereinafter). The washing-by-mixing method is advantageously carried out at least once, generally carried out twice to five times, preferably carried out twice to four times. In the washing-by-mixing method, the amount of water per part by weight of a liquid crystal per each washing time is 10 to 50 parts by weight, preferably 15 to 40 parts by weight.

The temperature for the washing treatment can be set around room temperature, generally preferably in the range of from 10 to 30° C. The washing time is required to be long enough to fully bring a liquid crystal into contact with water, and the total washing time is required to be about 15 minutes or longer. The washing for a long time is of no use, and the washing for up to 30 minutes is sufficient.

When the above washing treatment of a liquid crystal with water is carried out, two separated phases of an aqueous phase and a liquid crystal solution phase (organic phase) are formed, and the liquid crystal solution is obtained by separating out the aqueous phase. The liquid crystal solution is fed to the step 2. When alumina or silica gel is used as an adsorbent in the step 2, the above washing treatment with water can be omitted, and when the above washing treatment is carried out, preferably, water remaining in the solvent is removed as much as possible prior to the step 2.

In the step 2, the liquid crystal solution prepared in the above method is brought into contact with at least one adsorbent selected from the group consisting of zeolite, alumina and silica gel, to allow the adsorbent to mainly adsorb ionic impurities, which are thereby removed. By this contact treatment in the step 2, the amount of ionic impurities is remarkably decreased, and there can be obtained a liquid crystal having an improved specific resistance value.

The adsorbent used in the step 2 is zeolite, alumina or silica gel, and these adsorbents may be used alone or in combination. Of these adsorbents, zeolite is particularly preferred. Alumina may be any one of α-alumina, β-alumina or γ-alumina, while β-alumina is preferred.

When zeolite is used as an adsorbent in the step 2, the zeolite is desirably protonic type zeolite, particularly desirably $H^+$ type zeolite.

Further, zeolite having an $SiO_2/Al_2O_3$ molar ratio of 3/1 to 10/1 is suitable. In view of easiness in the procedures of separating zeolite from the solution after the contact treatment in step 2, the zeolite is desirably a columnar crystal having a diameter of 1 to 2 mm and a length of 0.5 to 1.5 mm.

In the step 2, the contact treatment of the liquid crystal solution with an adsorbent is not specially limited so long as these two are effectively brought into contact with each other. In view of industrial advantages, the contact treatment in the step 2 includes (i) a method in which an adsorbent is added to the liquid crystal solution and the mixture is stirred (mixing-by-stirring method) and (ii) a method in which the liquid crystal solution is allowed to pass through a column packed with an adsorbent (column method).

In the mixing-by-stirring method, the amount of the adsorbent per part by weight of a liquid crystal in the liquid crystal solution is 0.1 to 5 parts by weight, preferably 0.5 to 2 parts by weight, and the contact treatment time is 1 to 6 hours, preferably 2 to 5 hours. After the contact treatment by the mixing-by-stirring method is carried out, the adsorbent is separated by filtration, and the resultant liquid crystal solution is subjected to precision-filtration in the subsequent step 3.

When the column method is carried out in the step 2, the time (contact time) for which the liquid crystal solution passes through a column is generally 0.3 to 10 seconds, preferably 0.5 to 5 seconds. The liquid crystal solution which has passed through the column in the column method is precision-filtered in the following step 3 without subjecting it to additional treatment.

The contact treatment in the step 2 is carried out at a temperature of 10 to 50° C., preferably 20 to 30° C.

It is industrially advantageous to use a plurality of adsorbents in the above step 2. For example, the liquid crystal solution is contact-treated with alumina or silica gel, and then contact-treated with zeolite, whereby a liquid crystal having a higher purity can be obtained. In this case, a column packed with alumina or silica gel and a column packed with zeolite can be used, and the liquid crystal solution is allowed to pass through these columns. When a plurality of adsorbents are used in combination, the load on expensive zeolite can be decreased, which is advantageous.

Then, the liquid crystal solution separated from the adsorbent in the above step 2 is fed to the step 3 and subjected to the precision-filtration. In the step 3, fine particles of the adsorbent(s) used in the step 2 and other fine solid particles are removed. Prior to carrying out the precision filtration in the step 3, the liquid crystal solution may be filtered through a re-contamination-free filter having openings having ordinary diameters (e.g., filter paper), which filtration is desirable for decreasing a load on the precision filtration.

As a filter for the precision filtration, there is used a filter which is free from re-contamination and has micropores having a pore diameter of 0.1 to 0.3 µm. By the precision filtration, fine particles of the adsorbent and other fine particles are almost completely removed, and a liquid crystal having excellent thermal stability and a high specific resistance value can be obtained. The precision filtration is generally carried out at a temperature of 20 to 30° C.

The filtrate obtained by the precision filtration in the step 3 is fed to the step 4 where the solvent is removed, whereby a purified liquid crystal as an end product is obtained. The removal of the solvent is desirably carried out by distilling off the solvent. The condition of the distillation differs depending upon the kind of an aromatic hydrocarbon solvent. When the solvent is distilled off at too high a temperature, undesirably, the liquid crystal has deterioration by heat. Generally, the solvent is distilled off at a pressure of 50 to 200 Torr at a temperature of 40 to 70° C. After the solvent is distilled off, desirably, the liquid crystal is allowed to stand under high vacuum (e.g., 0.1 to 0.2 Torr and at the temperature of 50 to 100° C.) for 0.5 to 2 hours so that a trace amount of aromatic hydrocarbon solvent does not remain in the liquid crystal.

In the above procedures according to the present invention, there can be obtained a purified liquid crystal which shows a specific resistance value of at least $5 \times 10^{12}$ Ω·cm and a thermal decomposition ratio of 0.3% by weight or less, particularly 0.1% by weight or less.

EXAMPLES

Figure 1:
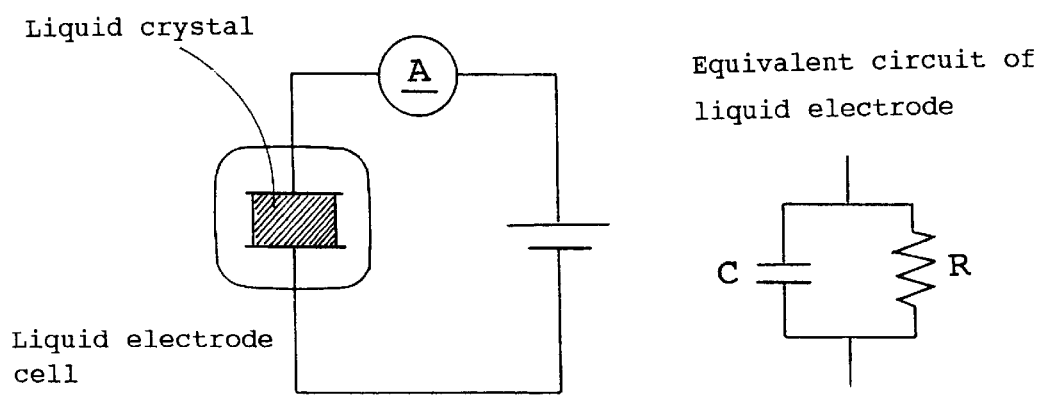
FIG. 1 schematically shows an electric circuit for explaining the measurement of a specific resistance value.

The present invention will be more specifically explained with reference to Examples and Comparative Examples hereinafter, while the present invention shall not be limited thereto.

In the following Examples and Comparative Examples, liquid crystals were measured or evaluated for specific resistance values and thermal stability (thermal decomposition ratios) by the following methods.

(1) Specific Resistance Value

A specific resistance value is determined by measuring a resistance R (Ω) by means of a circuit shown in FIG. 1. In the circuit, a liquid electrode cell works as a condenser. An electrode constant K (K=S/d=11.3*C, S=electrode area, d=electrode interval) is determined by measuring an electrostatic capacitance C (pF) when a liquid electrode cell is empty. Further, since substances to be measured were liquid crystal substances which are nearly in a solid state at room temperature, the liquid crystal substances were measured under the following conditions where ionic impurities are uniformly dispersed. 1 Gram of a substance to be measured was placed in a liquid electrode cell, and the mixture was heated to 100° C. in an oven and allowed to stand for 5 minutes to have an isotropic liquid crystal. Then, the mixture was gradually cooled to 25° C. and allowed to stand for 45 minutes, and the liquid crystal was measured for a resistance value.

(2) Thermal Stability Test

A liquid crystal was allowed to stand in air at 120° C. for 24 hours, and then analyzed by means of a high-performance liquid chromatography to determine a thermal decomposition ratio (%).

Comparative Example 1

An anti-ferroelectric liquid crystal having the following chemical formula (A) and having a specific resistance value of $6 \times 10^{10}$ Ω·cm was treated as follows.

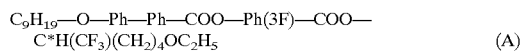

$$C_9H_{19}\text{—O—Ph—Ph—COO—Ph(3F)—COO—} \\ C^*H(CF_3)(CH_2)_4OC_2H_5 \quad (A)$$

wherein Ph is a 1,4-phenylene group, Ph(3F) is a 1,4-phenylene group in which fluorine is substituted on the 3-position designated from a hydroxyl group residue of the phenylene group, and C* is an asymmetric carbon atom.

1 Gram of a liquid crystal A was dissolved in 20 g of ultra-pure toluene. To the resultant solution was added 33 g of ultra-pure water having a specific resistance value of $1 \times 10^7$ Ω·cm, the mixture was shaken for 5 minutes, and then, the water was separated. Further, the above procedures were repeated twice to prepare a solution from which water was separated. To the solution was added 1 g of zeolite (supplied by Tosoh Corporation: USY HSG-330 HUD; $SiO_2/Al_2O_3=6/1$, average diameter 1.6 mm, average length 0.8 mm), and the mixture was stirred for 3 hours.

The solution was filtered from filter paper to separate the zeolite. Toluene was distilled off from the solution at a pressure of 100 Torr, and the resultant liquid crystal was treated at 90° C. under vacuum of 0.1 to 0.2 Torr for 1 hour.

Then, the above liquid crystal was measured for a specific resistance value and tested for thermal stability. Table 1 shows the results.

As shown in Table 1, the liquid crystal showed a greatly improved specific resistance value, while it was poor in thermal stability.

Example 1

The same solution as that obtained by filtering the zeolite off through the filter paper in Comparative Example 1 was further filtered through a filter which had 0.2 μm micropores and was made of Teflon. Thereafter, toluene was distilled off from the solution, and the resultant liquid crystal was further treated in the same manner as in Comparative Example 1.

Then, the above liquid crystal was measured for a specific resistance value and tested for thermal stability. Table 1 shows the results.

As shown in Table 1, the resultant liquid crystal showed a greatly improved specific resistance value and also showed excellent thermal stability.

Example 2

An anti-ferroelectric liquid crystal having the chemical formula (A) specified in Comparative Example 1 and having a specific resistance value of $6 \times 10^{10}$ $\Omega \cdot cm$ was treated as follows.

To a solution of 1 g of the liquid crystal in 20 g of ultra-pure toluene was added 1 g of zeolite (supplied by Tosoh Corporation: USY HSG-330 HUD; $SiO_2/Al_2O_3 = 6/1$, average diameter 1.6 mm, average length 0.8 mm), and the mixture was stirred for 3 hours. Then, the zeolite was filtered off through filter paper. Then, the toluene solution containing the liquid crystal was filtered through a filter made of Teflon having 0.2 μm micropores. Then, toluene was distilled off, and the resultant liquid crystal was treated at 90° C. under vacuum of 0.1 to 0.2 Torr for 1 hour. Then, the resultant liquid crystal was measured for a specific resistance value and tested for thermal stability. Table 1 shows the results.

TABLE 1

| | Specific resistance value ($\Omega \cdot cm$) | Thermal decomposition ratio (%) |
|---|---|---|
| Comparative Example 1 | $2 \times 10^{13}$ | 1.2 |
| Example 1 | $2 \times 10^{13}$ | 0.0 |
| Example 2 | $3 \times 10^{13}$ | 0.0 |

Comparative Example 2

An anti-ferroelectric liquid crystal compound (B) of the following chemical formula (B) was measured for a specific resistance value and tested for thermal stability. Table 2 shows the results.

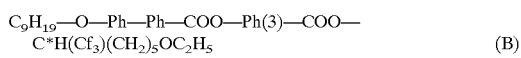

$$C_9H_{19}-O-Ph-Ph-COO-Ph(3)-COO-C*H(Cf_3)(CH_2)_5OC_2H_5 \quad (B)$$

wherein —Ph— is a 1,4-phenylene group, —Ph(3F)— is a 1,4-phenylene group in which fluorine is substituted on the 3-position designated from a hydroxyl group residue of the phenylene group, and C* is an asymmetric carbon atom.

Comparative Example 3

1.6 Grams of the liquid crystal of the formula (B) used in Comparative Example 2 was dissolved in 28 g of toluene to prepare a liquid crystal solution.

The liquid crystal solution was allowed to flow through column packed with 16 g of zeolite (supplied by Tosoh Corporation: USY HSG-330HUD; $SiO_2/Al_2O_3 \times 6/1$, average diameter 1.6 mm, average length 0.8 mm), at a flow rate of 8.8 g/second. In this case, the contact time of the liquid crystal solution was 1.8 seconds.

Toluene was distilled off from the eluated solution, and the resultant liquid crystal was measured for a specific resistance value and tested for thermal stability in the same manner as in Comparative Example 2. Table 2 shows the results.

The above liquid crystal had an improved specific resistance value, while it was not improved in resistance to thermal decomposition.

Example 3

The same eluated solution as that obtained in Comparative Example 3 was filtered through a filter made of Teflon having 0.2 μm micropores. Then, toluene was distilled off from the filtrate, and the resultant liquid crystal was measured for a specific resistance value, and tested for thermal stability, in the same manner as in Comparative Example 3. Table 2 shows the results.

The above liquid crystal showed an improved specific, resistance value and improved thermal stability.

Example 4

Example 2 was repeated except that the contact time was changed to 0.9 seconds. Table 2 shows the results.

Comparative Example 4

Example 3 was repeated except that the zeolite was replaced with molecular sieve 4A. Table 2 shows the results.

The liquid crystal was improved in specific resistance value but was not improved in thermal stability.

Comparative Example 5

A ferrielectric liquid crystal compound having the following chemical formula (C) was measured for a specific resistance value, and tested for thermal stability, in the same manner as in Comparative Example 2. Table 2 shows the results.

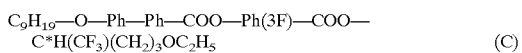

$$C_9H_{19}-O-Ph-Ph-COO-Ph(3F)-COO-C*H(CF_3)(CH_2)_3OC_2H_5 \quad (C)$$

wherein —Ph— is a 1,4-phenylene group, —Ph(3F)— is a 1,4-phenylene group in which fluorine is substituted on the 3-position designated from a hydroxyl group residue of the phenylene group, and C* is an asymmetric carbon atom.

Example 5

The same ferrielectric liquid crystal compound of the formula (C) as that used in Comparative Example 5 was treated in the same manner as in Example 3, and the resultant liquid crystal was measured for a specific resistance value and tested for thermal stability. Table 2 shows the results.

TABLE 2

| | Contact time (second) | Precision filtration | Specific resistance value (Ω · cm) | Thermal decomposition ratio (%) |
|---|---|---|---|---|
| CEx. 2 | — | No | $6 \times 10^{12}$ | 1.2 |
| CEx. 3 | 1.8 | No | $2 \times 10^{13}$ | 1.2 |
| Ex. 3 | 1.8 | Yes | $2 \times 10^{13}$ | 0 |
| Ex. 4 | 0.9 | Yes | $2 \times 10^{13}$ | 0 |
| CEx. 4 | 1.8 | Yes | $1 \times 10^{13}$ | 0.3 |
| CEx. 5 | — | No | $8 \times 10^{11}$ | 1.5 |
| Ex. 5 | 1.8 | Yes | $5 \times 10^{12}$ | 0 |

Ex. = Example, CEX. = Comparative Example

Examples 6 and 7

Purified liquid crystals were obtained in the same manner as in Example 2 except that the zeolite was replaced with alumina (Example 6) or silica gel (Example 7). The above alumina was activated alumina AC-11 (supplied by Sumitomo Chemical Co., Ltd., central particle diameter 80 to 100 μm), and the above silica gel was FL60B (supplied by Fuji Silysia Co., Ltd, particle diameter 60 μm). Table 3 shows the results.

TABLE 3

| | Specific resistance value (Ω · cm) | Thermal decomposition ratio (%) |
|---|---|---|
| Example 6 | $3 \times 10^{13}$ | 0.3 |
| Example 7 | $3 \times 10^{13}$ | 0.3 |

Examples 8 and 9

Purified liquid crystals were obtained in the same manner as in Example 1 except that the toluene was replaced with benzene (Example 8) or o-xylene (Example 9). Table 4 shows the results.

TABLE 4

| | Specific resistance value (Ω · cm) | Thermal decomposition ratio (%) |
|---|---|---|
| Example 8 | $2 \times 10^{13}$ | 0 |
| Example 9 | $2 \times 10^{13}$ | 0 |

What is claimed is:

1. A process for purifying a liquid crystal, which comprises preparing a first liquid crystal solution of an antiferroelectric liquid crystal or a ferrielectric liquid crystal to be purified in an aromatic hydrocarbon solvent, bringing the first liquid crystal solution into contact with zeolite, and then separating the zeolite therefrom to form a second liquid crystal solution, precision-filtering the so-obtained second liquid crystal solution to obtain a filtrate, and removing the solvent from the so-obtained filtrate and recovering a purified liquid crystal.

2. The process of claim 1, wherein the zeolite is protonic zeolite.

3. The process of claim 1, wherein the zeolite is a columnar zeolite having a diameter of 1 to 2 mm and a length of 0.5 to 1.5 mm.

4. The process of claim 1, wherein the aromatic hydrocarbon solvent is benzene, toluene or xylene.

5. The process of claim 1, wherein the aromatic hydrocarbon solvent is toluene.

6. The process of claim 1, wherein the precision-filtration is carried out using a filter having micropores having a pore diameter of 0.1 to 0.3 μm.

7. The process of claim 1, wherein the first liquid crystal solution is subjected to a washing treatment with pure water, said pure water having a specific resistance value of at least $1 \times 10^7$ Ω·cm, prior to contact with the zeolite.

8. The process of claim 7, wherein the pure water is used in an amount of 10 to 50 parts by weight per part by weight of the liquid crystal each washing treatment.

9. The process of claim 7, wherein the washing treatment is carried out at a temperature of 10 to 30° C.

10. The process of claim 7, wherein the washing treatment is carried out for a total time of at least 15 minutes.

11. The process of claim 1, which produces a liquid crystal having a specific resistance value of at least $5 \times 10^{12}$ Ω·cm and a thermal decomposition ratio of 0.3% by weight or less.

* * * * *